United States Patent [19]
Kleemann et al.

[11] Patent Number: 5,968,978
[45] Date of Patent: Oct. 19, 1999

[54] BIPHENYLSULFONYLCYANAMIDES, PROCESS FOR THEIR PREPARATION, AND THEIR USE AS MEDICAMENT

[75] Inventors: Heinz-Werner Kleemann, Bischofsheim; Jan-Robert Schwark, Kelkheim; Sabine Faber, Idstein; Hans Jochen Lang, Hofheim; Andreas Weichert, Egelsbach; Hans-Willi Jansen, Niedernhausen, all of Germany

[73] Assignee: Hoechst Marion Roussel Deutschland, Frankfurt am Main, Germany

[21] Appl. No.: 09/157,589

[22] Filed: Sep. 21, 1998

[30] Foreign Application Priority Data

Sep. 22, 1997 [DE] Germany .................. 197 41 635

[51] Int. Cl.⁶ ............... A61K 31/275; C07C 255/33; C07C 309/29
[52] U.S. Cl. .............. 514/524; 514/602; 514/604; 558/409; 558/408; 564/86; 564/87; 564/88; 564/91
[58] Field of Search ................ 514/524, 602, 514/604; 564/86, 87, 88, 91; 558/409, 408

[56] References Cited

U.S. PATENT DOCUMENTS

| | | | |
|---|---|---|---|
| 5,281,614 | 1/1994 | Ashton et al. | 514/359 |
| 5,412,097 | 5/1995 | Chakravarty et al. | 546/118 |

FOREIGN PATENT DOCUMENTS 0 855 392 A2  7/1998  European Pat. Off. .

OTHER PUBLICATIONS

George Wittig et al., "Methylenecyclohexane (Cyclohexane, methylene–)," *Organic Syntheses*, vol. 40, pp. 66–68. (1973).

Richard Greenwald, et al., "The Wittig Reaction Using Methylsulfinyl Carbanion–Dimethyl Sulfoxide," *J. Org. Chem.* (1963), vol. 28, pp. 1128–1129.

George Wittig et al., "Methylenecyclohexane" (Cyclohexane, methylene–), *Organic Syntheses*, vol. 5, (1973), pp. 751–754.

Heiner Jendralla et al., "Efficient, Simple Procedures for the Large–Scale Preparation of Building Blocks for Angiotensin (II) Receptor Antagonists," *Liebigs Ann.*, 1995, pp. 1253–1257.

*Primary Examiner*—Johann Richter
*Assistant Examiner*—Ebenezer Sackey
*Attorney, Agent, or Firm*—Finnegan, Henderson, Farabow, Garrett & Dunner, L.L.P.

[57] ABSTRACT

Compounds of the formula I

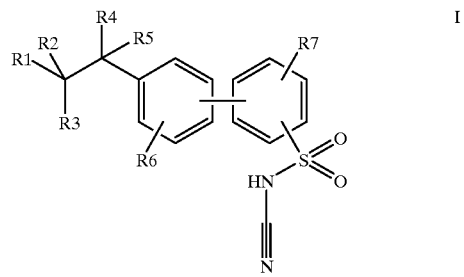

in which the symbols have the meanings indicated in the claims, have outstanding antiarrhythmic properties. They exhibit a cardioprotective component. They can inhibit or greatly decrease, in a preventive manner, the pathophysiological processes in the formation of ischemically induced damage, in particular in the elicitation of ischemically induced cardiac arrhythmias. Moreover, they have a strong inhibitory action on the proliferation of cells.

18 Claims, No Drawings

BIPHENYLSULFONYLCYANAMIDES, PROCESS FOR THEIR PREPARATION, AND THEIR USE AS MEDICAMENT

The invention relates to compounds of the formula (I),

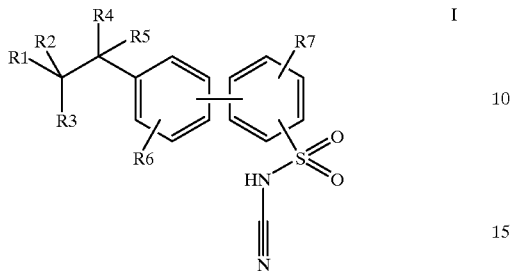

in which the symbols have the following meaning:

R(1) is hydrogen, alkyl having 1,2,3,4,5,6,7, or 8 carbon atoms, 1-naphthyl, 2-naphthyl, —$C_aH_{2a}$-cycloalkyl having 3,4,5,6 or 7 carbon atoms, or —$C_aH_{2a}$-phenyl, where the phenyl moiety is unsubstituted or substituted by 1–3 substituents which are alkyl having 1,2,3,4,5,6,7, or 8 carbon atoms, F, Cl, Br, I, $CF_3$, $SO_nR(11)$, OR(17), NR(8)R(9), —C≡N, —$NO_2$ or CO—R(22);
  R(11) is alkyl having 1,2,3, or 4 carbon atoms or NR(20)R(21);
    R(20) and R(21) independently of one another are hydrogen or alkyl having 1,2,3, or 4 carbon atoms;
  R(17) is hydrogen or alkyl having 1,2,3, or 4 carbon atoms;
  R(8) and R(9) independently of one another are hydrogen or alkyl having 1,2,3, or 4 carbon atoms;
  R(22) is hydrogen, alkyl having 1,2,3,4,5,6,7, or 8 carbon atoms or OR(30);
    R(30) is hydrogen, alkyl having 1,2,3,4,5,6,7 or 8 carbon atoms;
  a is zero, 1, or 2;
  n is zero, 1, or 2; or
R(1) and R(3) together with the carbon atom bonded to them are cycloalkyl having 3, 4, 5, 6 or 7 carbon atoms or fluorenyl;
R(2), R(3), R(4) and R(5) independently of one another are hydrogen, F, $CF_3$, O—R(10), alkyl having 1,2,3,4, 5,6,7, or 8 carbon atoms, cycloalkyl having 3, 4, 5, 6 or 7 carbon atoms, —$C_gH_{2g}$-phenyl, where the phenyl moiety is unsubstituted or substituted by 1–3 substituents which are F, Cl, Br, I, $CF_3$, methyl, methoxy, hydroxyl, or NR(18)R(19);
  R(18) and R(19) independently of one another are hydrogen or alkyl having 1,2,3, or 4 carbon atoms;
  g is zero, 1 or 2;
  R(10) is hydrogen, alkyl having 1,2,3,4,5,6,7 or 8 carbon atoms, phenyl which is unsubstituted or substituted by 1–3 substituents which are of F, Cl, Br, I, $CF_3$, methyl, methoxy, hydroxyl, or NR(12)R(13);
    R(12) and R(13) independently of one another are hydrogen or alkyl having 1,2,3, or 4 carbon atoms; or
  R(10) is heteroaryl having 1,2,3,4,5,6,7,8, or 9 carbon atoms, which is unsubstituted or substituted by 1–3 substituents which are F, Cl, Br, I, $CF_3$, $CH_3$, methoxy, hydroxyl or NR(14)R(15);
    R(14) and R(15) independently of one another are hydrogen or alkyl having 1,2,3, or 4 carbon atoms; or R(2) and R(4) together are a second bond between the carbon atoms bonded to the radicals R(3) and R(5), where R(1), R(3), and R(5) are as defined above;
R(6) and R(7) independently of one another are hydrogen, F, Cl, Br, I, $CF_3$, —C≡N, —$NO_2$, $SO_p$—R(16), CO—R(23), or O—R(24);
  R(23) is hydrogen, alkyl having 1,2,3,4,5,6,7, or 8 carbon atoms or OR(25);
    R(25) is hydrogen, alkyl having 1,2,3,4,5,6,7 or 8 carbon atoms;
  R(24) is hydrogen, alkyl having 1,2,3,4,5,6,7, or 8 carbon atoms or phenyl, which is unsubstituted or substituted by 1–3 substituents which are F, Cl, Br, I, $CF_3$, methyl, methoxy, hydroxyl or NR(28)R(29);
    R(28) and R(29) are H or alkyl having 1,2,3, or 4 carbon atoms;
  R(16) is alkyl having 1,2,3,4,5,6,7 or 8 carbon atoms, phenyl which is unsubstituted or substituted by 1–3 substituents which are F, Cl, Br, I, $CF_3$, methyl, methoxy, hydroxyl, or NR(26)R(27);
    R(26) and R(27) are H or alkyl having 1,2,3, or 4 carbon atoms;
  p is zero, 1, or 2;

and their physiologically tolerable salts.

Preferred compounds of the formula (I) are those where

R(1) is hydrogen, alkyl having 1,2,3 or 4 carbon atoms, 1-naphthyl, 2-naphthyl, —$C_aH_{2a}$-cycloalkyl having 3, 4, 5, 6 or 7 carbon atoms or —$C_aH_{2a}$-phenyl, where the phenyl moiety is unsubstituted or substituted by 1–2 substituents which are alkyl having 1,2,3 or 4 carbon atoms, F, Cl, $CF_3$, $SO_nR(11)$, OR(17), NR(8)R(9), —C≡N, or CO—R(22);
  R(11) is alkyl having 1,2,3, or 4 carbon atoms, or NR(20)R(21);
    R(20) and R(21) independently of one another are hydrogen, methyl, or ethyl;
  R(17) is hydrogen or alkyl having 1,2,3, or 4 carbon atoms;
  R(8) and R(9) independently of one another are hydrogen, methyl, or ethyl;
  R(22) is hydrogen, alkyl having 1,2,3, or 4 carbon atoms, or OR(30);
    R(30) is hydrogen, alkyl having 1,2,3, or 4 carbon atoms;
  a is zero or 1;
  n is zero or 2; or
R(1) and R(3) together with the carbon atom bonded to them are cycloalkyl having 3, 4, 5, 6 or 7 carbon atoms or fluorenyl;
R(2) and R(4) independently of one another are hydrogen or F; or
R(2) and R(4) together are a second bond between the carbon atoms bonded to the radicals R(3) and R(5);
R(3) and R(5) independently of one another are hydrogen, F, $CF_3$, O—R(10), alkyl having 1,2,3, or 4 carbon atoms, cycloalkyl having 3, 4, 5, 6, or 7 carbon atoms, —$C_gH_{2g}$-phenyl, where the phenyl moiety is unsubstituted or substituted by 1–2 substituents which are F, Cl, $CF_3$, methyl, methoxy, hydroxyl or NR(18)R(19);
  R(18) and R(19) independently of one another are hydrogen, methyl or ethyl;
  g is zero or 1;
  R(10) is hydrogen, alkyl having 1, 2, 3 or 4 carbon atoms, phenyl which is unsubstituted or substituted by 1–2 substituents which are of F, Cl, $CF_3$, methyl, methoxy, hydroxyl, or NR(12)R(13);

R(12) and R(13) independently of one another are hydrogen, methyl, or ethyl; or

R(10) is heteroaryl having 1, 2, 3, 4, 5, 6, 7, 8 or 9 carbon atoms, which is unsubstituted or substituted by 1–2 substituents which are F, Cl, $CF_3$, $CH_3$, methoxy, hydroxyl, or NR(14)R(15);

R(14) and R(15) independently of one another are hydrogen, ethyl, or ethyl;

R(6) and R(7) independently of one another are hydrogen, F, Cl, $CF_3$, —C≡N, $SO_p$—R(16), CO—R(23), or O—R(24);

R(23) is hydrogen, alkyl having 1,2,3, or 4 carbon atoms or OR(25);

R(25) is hydrogen, alkyl having 1,2,3, or 4 carbon atoms;

R(24) is hydrogen, alkyl having 1,2,3, or 4 carbon atoms or phenyl which is unsubstituted or substituted by 1–2 substituents which are F, Cl, $CF_3$, methyl, methoxy, hydroxyl or NR(28)R(29);

R(28) and R(29) independently of one another are hydrogen, methyl, or ethyl;

R(16) is alkyl having 1,2,3 or 4 carbon atoms or phenyl which is unsubstituted or substituted by 1–2 substituents which are F, Cl, $CF_3$, methyl, methoxy, hydroxyl, or NR(26)R(27);

R(26) and R(27) independently of one another are hydrogen, methyl, or ethyl;

p is zero or 2;

and their physiologically tolerable salts.

Particularly preferred compounds of the formula (I) are those where

R(1) is methyl, ethyl, 1-naphthyl, 2-naphthyl, —$C_aH_{2a}$-cycloalkyl having 3, 4, 5, 6 or 7 carbon atoms or —$C_aH_{2a}$-phenyl, where the phenyl moiety is unsubstituted or substituted by 1–2 substituents which are alkyl having 1,2,3, or 4 carbon atoms, F, Cl, $CF_3$, $SO_2R(11)$, OR(17), NR(8)R(9), —C≡N, or CO—R(22);

R(11) is methyl or dimethylamino;

R(17) is hydrogen, methyl, or ethyl;

R(8) and R(9) independently of one another are hydrogen, methyl, or ethyl,

R(22) is hydrogen or alkyl having 1,2,3, or 4 carbon atoms;

a is zero or 1; or

R(1) and R(3) together with the carbon atom bonded to them are cycloalkyl having 3,4,5,6, or 7 carbon atoms or fluorenyl;

R(2) and R(4) independently of one another are hydrogen or F; or

R(2) and R(4) together are a second bond between the carbon atoms bonded to radicals R(3) and R(5);

R(3) and R(5) independently of one another are hydrogen, F, $CF_3$, O—R(10), alkyl having 1,2,3 or 4 carbon atoms or —$C_gH_{2g}$-phenyl which is unsubstituted or substituted by 1–2 substituents which are F, Cl, $CF_3$, methyl, methoxy, hydroxyl or NR(18)R(19);

R(18) and R(19) independently of one another are hydrogen, methyl, or ethyl;

g is zero or 1;

R(10) is hydrogen, alkyl having 1,2,3 or 4 carbon atoms or phenyl which is unsubstituted or substituted by 1–2 substituents which are F, Cl, $CF_3$, methyl, methoxy, hydroxyl, or NR(12)R(13);

R(12) and R(13) are hydrogen, methyl, or ethyl; or

R(10) is heteroaryl having 1,2,3,4,5,6,7,8, or 9 carbon atoms, which is unsubstituted or substituted by 1–2 substituents which are F, Cl, $CF_3$, $CH_3$, methoxy, hydroxyl or dimethylamino;

R(6) and R(7) independently of one another are hydrogen, F, Cl, $CF_3$, —C≡N, $SO_2$—R(16), CO—R(23), or O—R(24);

R(23) is hydrogen or alkyl having 1, 2, 3, or 4 carbon atoms;

R(24) is hydrogen, alkyl having 1,2,3 or 4 carbon atoms or phenyl which is unsubstituted or substituted by 1–2 substituents which are F, Cl, $CF_3$, methyl, methoxy, hydroxyl, or NR(28)R(29);

R(28) and R(29) independently of one another are hydrogen, methyl, or ethyl;

R(16) is alkyl having 1,2,3 or 4 carbon atoms;

and their physiologically tolerable salts.

Very particularly preferred compounds of the formula (I) are those where

R(1) is methyl, ethyl, 1-naphthyl, 2-naphthyl, cycloalkyl having 3, 4, 5, 6 or 7 carbon atoms or phenyl which is unsubstituted or substituted by a substituent which is alkyl having 1,2,3, or 4 carbon atoms, F, Cl, $CF_3$, $SO_2R(11)$, OR(17), NR(8)R(9) or CO—R(22);

R(11) is methyl or dimethylamino;

R(17) is hydrogen, methyl, or ethyl;

R(8) and R(9) independently of one another are hydrogen, methyl, or ethyl;

R(22) is hydrogen or alkyl having 1,2,3, or 4 carbon atoms; or

R(1) and R(3) together with the carbon atom bonded to them are cycloalkyl having 3, 4, 5, 6, or 7 carbon atoms or fluorenyl;

R(2) and R(4) are hydrogen; or

R(2) and R(4) together are a second bond between the carbon atoms bonded to radicals R(3) and R(5);

R(3) and R(5) independently of one another are hydrogen, $CF_3$, O—R(10), alkyl having 1, 2, 3 or 4 carbon atoms or phenyl which is unsubstituted or substituted by a substituent which is F, Cl, $CF_3$, methyl, methoxy, hydroxyl or NR(18)R(19);

R(18) and R(19) independently of one another are hydrogen, methyl or ethyl;

R(10) is hydrogen, alkyl having 1,2,3 or 4 carbon atoms or phenyl which is unsubstituted or substituted by 1 substituent which is of F, Cl, $CF_3$, methyl, methoxy, hydroxyl, or NR(12)R(13);

R(12) and R(13) independently of one another are hydrogen, methyl, or ethyl, or

R(10) is heteroaryl having 1, 2, 3, 4, 5, 6, 7, 8, or 9 carbon atoms, which is unsubstituted or substituted by a substituent which is F, Cl, $CF_3$, $CH_3$, methoxy, hydroxyl, or dimethylamino;

R(6) and R(7) independently of one another are hydrogen, F, Cl, $CF_3$, $SO_2$—$CH_3$, CO—R(23), or O—R(24);

R(23) is hydrogen or alkyl having 1,2,3, or 4 carbon atoms;

R(24) is hydrogen, alkyl having 1,2,3 or 4 carbon atoms or phenyl which is unsubstituted or substituted by 1 substituent which is F, Cl, $CF_3$, methyl, methoxy, hydroxyl or NR(28)R(29);

R(28) and R(29) independently of one another are hydrogen, methyl, or ethyl;

and their physiologically tolerable salts.

Preferred compounds of the formula I are also those in which the biphenyl ring is linked as in compounds of the formula

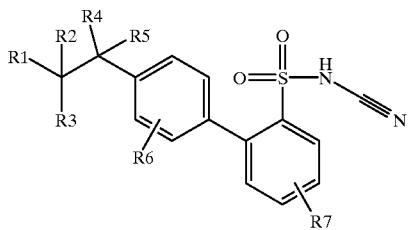

and the sulfonylcyanamide group is located in the 2 position.

Preferred compounds of the formula I are furthermore those in which R(3) and R(5) are hydrogen and R(2) and R(4) are also hydrogen or together are a bond.

Furthermore, compounds of the formula I are preferred in which R(1) and R(3) together with the carbon atom carrying them are cycloalkyl having 3,4,5,6 or 7 carbon atoms.

Preferred compounds of the formula I are also those in which R(1) is phenyl which is preferably unsubstituted or is substituted by a substituent which is alkyl having 1,2,3 or 4 carbon atoms, F, Cl, CF$_3$, SO$_2$R(11), OR(17), NR(8)R(9), or CO—R(22);

R(11) is methyl or dimethylamino;

R(17) is hydrogen, methyl, or ethyl;

R(8) and R(9) independently of one another are hydrogen, methyl, or ethyl;

R(22) is hydrogen or alkyl having 1,2,3. or 4 carbon atoms.

Preferred compounds of the formula I are those in which R(6) and R(7) are hydrogen.

Alkyl can be straight-chain or branched.

Cycloalkyl is also understood as meaning alkyl-substituted rings.

Examples of alkyl radicals having 1, 2, 3, 4, 5, 6, 7, or 8 carbon atoms are: methyl, ethyl, propyl, butyl, pentyl, hexyl, heptyl, octyl, isopropyl, isobutyl, isopentyl, neopentyl, isohexyl, 3-methylpentyl, sec-butyl, tert-butyl, and tert-pentyl.

Cycloalkyl radicals are, in particular, cyclopropyl, cyclobutyl, cyclopentyl, cyclohexyl, cycloheptyl, which, however, can also be substituted, for example, by alkyl having 1, 2, 3, or 4 carbon atoms. As an example of substituted cycloalkyl radicals, 4-methylcyclohexyl and 2,3-dimethylcyclopentyl may be mentioned.

Heteroaryl having 1,2,3,4,5,6,7,8 or 9 carbon atoms is understood as meaning, in particular, radicals which are derived from phenyl or naphthyl, in which one or more CH groups are replaced by N and/or in which at least two adjacent CH groups are replaced by S, NH, or O (with formation of a five-membered aromatic ring). In addition, one or both atoms of the condensation site of bicyclic radicals can also be nitrogen atoms (such as in indolizinyl).

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, and cinnolinyl.

Stereocenters which may occur can have either the (R) or (S) configuration.

Physiologically tolerable salts of compounds of the formula (I) are understood as meaning both their organic and inorganic salts, such as are described in Remington's Pharmaceutical Sciences (17th Edition, page 1418 (1985)). On account of their physical and chemical stability, and solubility, for acidic groups, inter alia, sodium, potassium, calcium, and ammonium salts are preferred; for basic groups, inter alia, salts of hydrochloric acid, sulfuric acid, phosphoric acid or of carboxylic acids, or sulfonic acids, such as, for example, acetic acid, citric acid, benzoic acid, maleic acid, fumaric acid, tartaric acid and p-toluenesulfonic acid are preferred.

The invention also relates to a process for the preparation of the novel compounds of the formula (I), and their physiologically tolerable salts, which comprises reacting compounds of the formula (II)

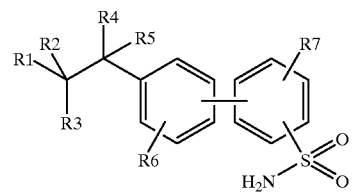

in which the radicals are as defined above, with cyanogen bromide. The reaction is expediently carried out in a dipolar aprotic solvent which is stable to cyanogen bromide, for example acetonitrile, DMA, TMU or NMP using a strong auxiliary base which is not very nucleophilic, such as, for example, K$_2$CO$_3$ or Cs$_2$CO$_3$. A suitable reaction temperature is a temperature between 0° C. and the boiling point of the solvent used; a temperature between 60° C. and 120° C. is preferred.

Compounds of the formula II can be prepared by a Wittig reaction of a compound of the formula III

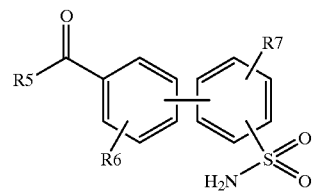

in which R(5), R(6) and R(7) are as defined above and which can be prepared, for example, as described in Liebigs Ann. 1995 1253, with a phosphorane which contains the radicals R(1) and/or R(2) and/or R(3). Such Wittig reactions are known to the person skilled in the art and are described, for example, in Org. Synth. 1960, 40, 66; J. Org. Chem. 1963, 28, 1128 and Org. Synth. Coll. Vol. 5 1973, 751.

The compounds of the formula I according to the invention are suitable as inhibitors of the sodium-dependent bicarbonate/chloride exchanger (NCBE) or of the sodium/bicarbonate symporter.

In EP-A 855 392, imidazole derivatives having a biphenylsulfonylcyanamide side chain have been proposed as NCBE inhibitors.

In addition, the invention relates to the use of a compound of the formula I for the production of a medicament for the treatment or prophylaxis of illnesses caused by ischemic conditions;

and the use of a compound of the formula I for the production of a medicament for the treatment or prophylaxis of cardiac infarction;

and the use of a compound of the formula I for the production of a medicament for the treatment or prophylaxis of angina pectoris;

and the use of a compound for the formula I for the production of a medicament for the treatment or prophylaxis of ischemic conditions of the heart;

and the use of a compound of the formula I for the production of a medicament for the treatment or prophylaxis of ischemic conditions of the peripheral and central nervous system and of stroke;

and the use of a compound of the formula I for the production of a medicament for the treatment or prophylaxis of ischemic conditions of peripheral organs and members;

and the use of a compound of the formula I for the production of a medicament for the treatment of states of shock;

and the use of a compound of the formula I for the production of a medicament for use in surgical operations and organ transplantations;

and the use of a compound of the formula I for the production of a medicament for the preservation and storage of transplants for surgical measures;

and the use of a compound of the formula I for the production of a medicament for the treatment of illnesses in which cell proliferation is a primary or secondary cause; and thus its use for the production of an antiatherosclerotic, an agent against diabetic late complications, carcinomatous disorders, fibrotic disorders such as pulmonary fibrosis, liver fibrosis or kidney fibrosis, prostate hyperplasia;

and the use of a compound of the formula I for the production of a medicament for the treatment of impaired respiratory drive;

and a pharmaceutical comprising an efficacious amount of a compound of the formula I.

The compounds of the formula (I) according to the invention exhibit very good antiarrhythmic properties, such as are important, for example, for the treatment of illnesses which occur in the case of oxygen deficiency symptoms. On account of their pharmacological properties, the compounds of the formula (I) are outstandingly suitable as antiarrhythmic pharmaceuticals having a cardioprotective component for infarct prophylaxis and infarct treatment and for the treatment of angina pectoris, where they also inhibit or greatly decrease, in a preventive manner, the pathophysiological processes in the formation of ischemically induced damage, in particular in the elicitation of ischemically induced cardiac arrhythmias. Because of their protective actions against pathological hypoxic and ischemic situations, the compounds of the formula (I) according to the invention can be used, on account of inhibition of the cellular $Na^+$-dependent $Cl^-/HCO_3^-$ exchange mechanism (=NCBE inhibitors) or of the sodium/bicarbonate symporter as pharmaceuticals for the treatment of all acute or chronic damage caused by ischemia or illnesses induced primarily or secondarily thereby. They protect organs acutely or chronically undersupplied with oxygen by lowering or preventing ischemically induced damage and are thus suitable as pharmaceuticals, for example, in thromboses, vascular spasms, atherosclerosis, or in surgical interventions (e.g. in liver and kidney organ transplantations, where the compounds can be used both for the protection of the kidneys in the donor before and during removal, for the protection of removed organs, for example during treatment with or storage thereof in physiological bath fluids, and during transfer to the recipient's body) or chronic or acute kidney failure.

The compounds of the formula (I) are also valuable pharmaceuticals having a protective action when carrying out angioplastic surgical interventions, for example on the heart and on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula (I) according to the invention are also suitable for the treatment of forms of shock, such as, for example, of allergic, cardiogenic, hypovolemic, and bacterial shock.

Moreover, the compounds of the formula (I) according to the invention are distinguished by strong inhibitory action on the proliferation of cells, for example on fibroblast cell proliferation and on the proliferation of the smooth vascular muscle cells. The compounds of the formula (I) are thus suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, liver fibrosis or kidney fibrosis, organ hypertrophies and hyperplasias, in particular in prostate hyperplasia or prostate hypertrophy.

It has been found that inhibitors of the $Na^+$-dependent $Cl^-/HCO_3^-$ exchanger (NCBE inhibitors) or of the sodium/bicarbonate symporter can stimulate the respiration by means of an increase in the chemosensitivity of the respiratory chemoreceptors. These chemoreceptors are responsible to a considerable extent for the maintenance of an orderly respiratory activity. They are activated in the body by hypoxia, pH decrease and increase in $CO_2$ hypercapnia) and result in an adjustment of the respiratory minute volume. During sleep, the respiration is particularly susceptible to interference and to a great extent dependent on the activity of the chemoreceptors. An improvement in the respiratory drive as a result of stimulation of the chemoreceptors with substances which inhibit the $Na^+$-dependent $Cl^-/HCO_3^-$ exchange results in an improvement of the respiration in the following clinical conditions and illnesses: impaired central respiratory drive (e.g. central sleep apnea, sudden infant death, post-operative hypoxia), muscle-related respiratory disorders, respiratory disorders after long-term ventilation, respiratory disorders during adaptation in a high mountain area, obstructive and mixed forms of sleep apneas, acute and chronic lung diseases with hypoxia and hypercapnia.

The compounds of the formula I according to the invention and their physiologically tolerable salts can be used in animals, preferably in mammals, and in particular in man, as pharmaceuticals per se, in mixtures with one another or in the form of pharmaceutical preparations. The present invention also relates to the compounds of the formula I and their physiologically tolerable salts for use as pharmaceuticals, their use in the therapy and prophylaxis of the syndromes mentioned and the production of medicaments therefor. The present invention furthermore relates to pharmaceutical preparations which as active constituents contain an efficacious dose of at least one compound of the formula I and/or of a physiologically tolerable salt thereof in addition to customary pharmaceutically innocuous excipients and auxiliaries. The pharmaceutical preparations normally contain 0.1 to 99 percent by weight, preferably 0.5 to 95 percent by weight, of the compounds of the formula I and/or their physiologically tolerable salts. The pharmaceutical preparations can be prepared in a manner known per se. To this end, the compounds of the formula I and/or their physiologically tolerable salts are brought, together with one or more solid or liquid pharmaceutical excipients and/or auxiliaries and, if desired, in combination with other pharmaceutical active compounds into a suitable administration form or dose form, which can then be used as a pharmaceutical in human medicine or veterinary medicine.

Pharmaceuticals which contain a compound of the formula (I) and/or its physiologically tolerable salts can be administered orally, parenterally, intravenously, rectally or by inhalation, the preferred administration being dependent on the particular symptoms of the disorder. The compounds of the formula I can be used here on their own or together with pharmaceutical auxiliaries, namely both in veterinary and in human medicine.

The person skilled in the art is familiar on the basis of his expert knowledge with the auxiliaries, which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, or colorants.

For an oral administration form, the active compounds are mixed with the additives suitable therefor, such as excipients, stabilizers, or inert diluents and are brought by means of the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. Preparation can take place here both as dry and as moist granules. Possible oily excipients or solvents are, for example, vegetable or animal oils, such as sunflower oil or codliver oil.

For subcutaneous or intravenous administration, the active compounds are brought into solution, suspension or emulsion, if desired with the substances customary therefor such as solubilizers, emulsifiers or other auxiliaries. Suitable solvents, for example, are: water, physiological saline solution or alcohols, e.g., ethanol, propanol, glycerol, and additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers, and also a propellant. Such a preparation customarily contains the active compound in a concentration from approximately 0.1 to 10%, in particular from approximately 0.3 to 3%, by weight.

The dose of the active compound of the formula (I) to be administered and the frequency of administration depend on the potency and duration of action of the compounds used; additionally also on the nature and severity of the illness to be treated and on the sex, age, weight, and individual responsiveness of the mammal to be treated.

On average, the daily dose of a compound of the formula I in a patient weighing approximately 75 kg is at least 0.001 mg/kg, preferably 0.01 mg/kg, to at most 10 mg/kg, preferably 1 mg/kg, of body weight. In acute episodes of the disease, for example immediately after suffering a cardiac infarct, even higher and, especially, more frequent doses may also be necessary, e.g., up to 4 individual doses per day. In particular on i.v. administration, for example in the case of an infarct patient in the intensive care unit, up to 200 mg per day may be necessary.

The compounds of the formula I and/or their physiologically tolerable salts can also be used to achieve an advantageous therapeutic action together with other pharmacologically active compounds for the treatment or prophylaxis of the abovementioned syndromes, in particular for the treatment of cardiovascular disorders. Combination with inhibitors of the sodium/hydrogen exchanger (NHE) and/or with active substances from other classes of cardiovascular active compound is preferred.

The invention additionally relates very generally to the combination of a) NCBE inhibitors and/or their physiologically tolerable salts with NHE inhibitors and/or their physiologically tolerable salts; b) NCBE inhibitors and/or their physiologically tolerable salts with active substances from other classes of cardiovascular active compound and/or their physiologically tolerable salts and c) of NCBE inhibitors and/or their physiologically tolerable salts with NHE inhibitors and/or their physiologically tolerable salts and with active substances from other classes of cardiovascular active compounds and/or their physiologically tolerable salts. Those combinations are preferred in which NCBE inhibitors of the formula I and/or their physiologically tolerable salts are used.

The active compounds known and identified as NHE inhibitors are guanidine derivatives, preferably acylguanidines, inter alia as are described in Edward J. Cragoe, Jr., "DIURETICS, Chemistry, Pharmacology and Medicine", J. WILEY & Sons (1983), 303–341 or the NHE inhibitors mentioned in DE19737224.4.

Suitable NHE inhibitors are, for example, also benzoylguanidines, such as are described in U.S. Pat. Nos. 5,292,755, 5,373,024, 5,364,868, 5,591,754, 5,516,805, 5,559,153, 5,571,842, 5,641,792, 5,631,293, EP-A 577024, EP-A602522, EP-A 602523, EP-A 603650, EP-A604852, EP-A 612723, EP-A 627413, EP-A 628543, EP-A 640593, EP-A 640588, EP-A702001, EP-A 713864, EP-A 723956, EP-A 754680, EP-A 765868, EP-A 774459, EP-A794171, DE 19624178.2, DE 19713427.0; ortho-substituted benzoylguanidines, such as are described in EP-A 556673, EP-A 791577, EP-A 794172, DE 19624178.2; ortho-amino-substituted benzoylguanidines, such as are described in EP-A 690048; isoquinolines, such as are described in EP-A 590455; benzo-fused 5-membered ring heterocycles, such as are described in EP-A 639573; diacyl-substituted guanidines, such as are described in EP-A 640587; acylguanidines, such as are described in U.S. Pat. No. 5,547,953; phenyl-substituted alkyl- or alkenylcarbonylguanidines carrying perfluoroalkyl groups, such as are described in U.S. Pat. No. 5,567,734, EP-A 688766; heteroaroylguanidines, such as are described in EP-A 676395; bicyclic heteroaroylguanidines, such as are described in EP-A 682017; indenoylguanidines, such as are described in EP-A 738712; benzyloxycarbonylguanidines, such as are described in EP-A 748795; phenyl-substituted alkenylcarbonylguanidines carrying fluorophenyl groups, such as are described in EP-A 744397; substituted cinnamoylguanidines, such as are described in EP-A 755919; sulfonimidamides, such as are described in EP-A 771788; benzenedicarbonyldiguanidines, such as are described in EP-A 774458, EP-A 774457; diarylcarbonyldiguanidines, such as are described in EP-A 787717; substituted thiophenylalkenylcarbonylguanidines, such as are described in EP-A 790245; bis-ortho-substituted benzoylguanidines, such as are described in DE 19621319.3; substituted 1- or 2-naphthylguanidines, such as are described in DE 19621482.3 and DE 19621483.1; indanylidineacetylguanidines, such as are described in EP 96112275.1; phenyl-substituted alkenylcarbonylguanidines, such as are described in DE 19633966.9; aminopiperidylbenzoylguanidines, such as are described in EP 667341; heterocycloxybenzylguanidines, such as are described in EP-A 694537; ortho-substituted benzoylguanidines, such as are described in EP704431; ortho-substituted alkylbenzylguanidines, such as are described in EP-A 699660; ortho-substituted heterocyclylbenzoylguanidines, such as are described in EP-A 699666; ortho-substituted 5-methylsulfonylbenzoylguanidines, such as are described in EP-A 708088; ortho-substituted 5-alkylsulfonylbenzoylguanidines having 4-amino substituents, such as are described in EP-A 723963; ortho-substituted 5-alkylsulfonylbenzoylguanidines having 4-mercapto substituents, such as are described in EP-A 743301; 4-sulfonyl- or 4-sulfinylbenzylguanidines, such as are described in EP-A 758644; alkenylbenzoylguanidines, such as are described in EP-A 760365; benzoylguanidines with fused, cyclic sulfones, such as are described in DE 19548708; benzoyl-, polycyclic aroyl- and heteroaroylguanidines, such as are described in WO 9426709; 3-aryl/heteroarylbenzoylguanidines, such as are described in WO 9604241; 3-phenylbenzoylguanidines having a basic amide in the 5-position, such as are described in WO 9725310; 3-dihalothienyl- or 3-dihalophenylbenzoylguanidines having a basic substituent in the 5-position, such as are described in WO 9727183; 3-9 methylsulfonylbenzoylguanidines having specific amino substituents in the 4-position, such as are described in WO 9512584; amiloride derivatives, such as are described in WO 9512592; 3-methylsulfonylbenzoylguanidines having specific amino substituents in the 4-position, such as are described in WO 9726253; indoloylguanidines, such as are described in EP-A 622356 and EP-A 708091; indoloylguanidines having a fused additional ring system, such as are described in EP 787728; methylguanidine derivatives, such as are described in WO 9504052; 1,4-benzoxazinoyl-guanidines, such as are described in EP-A 719766; 5-bromo-2-naphthoylguanidines, such as are described in JP 0225513; quinoline-4-carbonylguanidines having a phenyl radical in the 2-position, such as are described in EP-A 726254; cinnamoylguanidines, such as are described in JP 09059245; propenoylguanidines having a naphthalene substituent, such as are described in JP 9067332; propenoylguanidines having indole substituents, such as are described in JP 9067340; or heteroaryl-substituted acroylguanidines, such as are described in WO 9711055, and their physiologically tolerable salts.

Preferred NHE inhibitors are the compounds emphasized as preferred in the publications mentioned. Very particularly preferred compounds are cariporide (HOE642), HOE 694, EMD 96785, FR 168888, FR 183998, SM-20550, KBR-9032, and their physiologically tolerable salts. The most preferred is cariporide or another physiologically tolerable salt of N-(4-isopropyl-3-methanesulfonylbenzoyl) guanidine.

Examples of classes of active compound having cardiovascular activity which can therapeutically be advantageously combined with NCBE inhibitors or can additionally be combined with combinations of NCBE inhibitors and NHE inhibitors are beta-receptor blockers, calcium antagonists, angiotensin-converting enzyme inhibitors, angiotensin receptor blockers, loop diuretics, thiazide diuretics, potassium-sparing diuretics, aldosterone antagonists, such as are employed, for example, in lowering blood pressure, and also cardiac glycosides or other contractile force-increasing agents in the treatment of cardiac insufficiency and of congestive heart failure, as well as antiarrhythmics of the classes I–IV, nitrates, $K_{ATP}$ openers, $K_{ATP}$ blockers, inhibitors of the veratridine-activatable sodium channel, etc. Thus the following, for example, are suitable: the beta-blockers propanolol, atenolol, metoprolol; the calcium antagonists diltiazem hydrochloride, verapamil hydrochloride, nifedipine; the ACE inhibitors captopril, enalapril, ramipril, trandolapril, quinapril, spirapril, preferably ramipril or trandolapril; the angiotensin II receptor antagonists losartan, valsartan, telmisartan, eprosartan, tasosartan, candesartan, irbesartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glyceryl trinitrate; the $K^+(ATP)$ openers cromakalim, lemakalim, nocorandil, pinacidil, minoxidil; the inhibitors of the veratridine-activatable $Na^+$ channel.

Blockers of the noninactivating sodium channel (veratridine-activatable sodium channel) are an example of such a particularly advantageous combination component with NCBE inhibitors. The combinations of an NCBE inhibitor with a blocker of the noninactivating sodium channel (veratridine-activatable sodium channel) are suitable for infarction and reinfarction prophylaxis and treatment and also for the treatment of angina pectoris and the inhibition of ischemically induced cardiac arrhythmias, tachycardia and the origin and maintenance of ventricular fibrillation, the combinations of an NCBE inhibitor with a blocker of the noninactivating sodium channel also inhibiting or greatly decreasing, in a preventive manner, the pathophysiological processes in the formation of ischemically induced damage. Because of their increased protective actions against pathological hypoxic and ischemic situations, the novel combinations of an NCBE inhibitor with a blocker of the noninactivating sodium channel can be used, as a result of increased inhibition of the $Na^+$ influx into the cell, as pharmaceuticals for the treatment of all acute or chronic damage caused by ischemia or illnesses primarily or secondarily induced thereby. This relates to their use as pharmaceuticals for surgical interventions, e.g., in organ transplantation, where the combinations of an NCBE inhibitor with a blocker of the noninactivating sodium channel can be used both for the protection of the organs in the donor before and during removal, for the protection of removed organs, for example even during storage thereof in physiological bath fluids, and during transfer to the recipient's body. The combinations of an NCBE inhibitor with a blocker of the noninactivating sodium channel are also valuable pharmaceuticals having a protective action when carrying out angioplastic surgical interventions, for example on the heart and also on peripheral vessels. Corresponding to their protective action against ischemically induced damage, the combinations of an NCBE inhibitor with a blocker of the noninactivating sodium channel are also suitable as pharmaceuticals for the treatment of ischemias of the nervous system, in particular of the central nervous system, where they are suitable for the treatment of stroke or of cerebral edema. Moreover, the novel combinations of an NCBE inhibitor with a blocker of the noninactivating sodium channel are also suitable for the treatment of forms of shock, such as, for example, of allergic, cardiogenic, hypovolemic and of bacterial shock.

In addition to administration as a fixed combination, the invention also relates to the simultaneous, separate or sequential administration of NCBE inhibitors with NHE inhibitors and/or of an additional active substance from another class of cardiovascular active compounds for the treatment of the abovementioned illnesses.

The invention additionally relates to a pharmaceutical preparation comprising a) an NCBE inhibitor and an NHE inhibitor and/or their physiologically tolerable salts; or b) an NCBE inhibitor and additionally an active substance from another class of cardiovascular active compound and/or their physiologically tolerable salts; or c) an NCBE inhibitor, an NHE inhibitor and additionally an active substance from another class of cardiovascular active compound, and/or their physiologically tolerable salts.

Pharmaceutical preparations which contain a compound of the formula I and/or its physiologically tolerable salt as an NCBE inhibitor are preferred.

By means of combined administration, the effect of one combination component can be potentiated by the other respective component, i.e. the action and/or duration of action of a novel combination or preparation is stronger or longer lasting than the action and/or duration of action of the respective individual components (synergistic effect). This leads on combined administration to a reduction of the dose of the respective combination component, compared with individual administration. The novel combinations and preparations accordingly have the advantage that the amounts of active compound to be administered can be significantly reduced and undesired side effects can be eliminated or greatly reduced.

The invention furthermore relates to a commercial pack comprising as pharmaceutical active compound a) an NCBE inhibitor and an NHE inhibitor and/or their physiologically tolerable salts; or b) an NCBE inhibitor and additionally an active substance from another class of cardiovascular active compound and/or their physiologically tolerable salts; or c) an NCBE inhibitor, an NHE inhibitor and additionally an active substance from another class of cardiovascular active compound and/or their physiologically tolerable salts, in each case together with instructions for the use of these active compounds in combination for simultaneous, separate or sequential administration in the treatment or prophylaxis of the abovementioned syndromes, in particular for the treatment of cardiovascular disorders.

Commercial packs which contain compounds of the formula I as NCBE inhibitors are preferred.

The pharmaceutical preparations according to the invention can be prepared, for example, by either intensively mixing the individual components as a powder, or by dissolving the individual components in the suitable solvent such as, for example, a lower alcohol and then removing the solvent.

The weight ratio of the NCBE inhibitor to the NHE inhibitor or the substance having cardiovascular activity in the novel combinations and preparations is expediently 1:0.01 to 1:100, preferably 1:0.1 to 1:10.

The novel combinations and preparations in total contain preferably 0.5–99.5% by weight, in particular 4–99% by weight, of these active compounds.

When used according to the invention in mammals, preferably in man, the doses of the various active compound components, for example, vary in the range from 0.001 to 100 mg/kg/day.

List of abbreviations:
Bn Benzyl
$CH_2Cl_2$ Dichloromethane
DCI Desorption Chemical Ionization
DIP Diisopropyl ether
DMA Dimethylacetamide
DME Dimethoxyethane
DMF N,N-Dimethylformamide
EA Ethyl acetate (EtOAc)
EI electron impact
eq equivalent
ES Electrospray ionization
Esneg Electrospray, negative ionization
Et Ethyl
EtOH Ethanol
FAB Fast Atom Bombardment
HEP n-Heptane
HOAc Acetic acid
KotBu Potassium t-butoxide
Me Methyl
MeOH Methanol
mp melting point
MTB Methyl tertiary-butyl ether
NCBE Sodium-dependent chloride/bicarbonate exchanger
NHE Sodium/hydrogen exchanger
NMP N-Methylpyrrolidone
RT room temperature
THF Tetrahydrofuran
TMU N,N,N',N'-Tetramethylurea
Tol Toluene
CNS Central nervous system General procedure for the preparation of sulfonylcyanamides from sulfonamides The sulfonamide starting material is dissolved in 10 ml/mmol of anhydrous acetonitrile, 3 mol equivalents of $K_2CO_3$ and one mol equivalent of a 5 N solution of BrCN in acetonitrile are added dropwise and the mixture is heated under reflux until conversion is complete (typical reaction time 10 minutes to 6 hours). The reaction mixture is then chromatographed on silica gel without further working up after cooling to RT.

EXAMPLE 1

4'-Cyclohexylidenemethylbiphenyl-2-sulfonylcyanamide

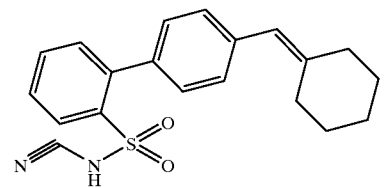

a) 4'-Formylbiphenyl-2-sulfonamide 5.0 g of N-dimethylaminomethylene-4'-formylbiphenyl-2-sulfonamide (Liebigs Ann. 1995, 1253) were dissolved in 50 ml of EtOH, treated with 50 ml of a saturated aqueous HCl solution and refluxed for 2 h. The mixture was then cooled to RT, 500 ml of water were added, the mixture was stirred for 2 h and the product was filtered off with suction. It was recrystallized from MTB and 2.8 g of white crystals were obtained, mp 165° C. (with decomposition).

$R_f$(MTB)=0.57 MS(DCI): 262(M+1)$^+$ b) 4'-Cyclohexylidenemethylbiphenyl-2-sulfonamide 5.5 g of cyclohexyltriphenylphosphonium bromide and 2.6 g of KOtBu were stirred at RT for 4 h in 200 ml of anhydrous THF. 3.0 g of 4'-formylbiphenyl-2-sulfonamide were added and the mixture was stirred at RT for 18 h. It was then diluted with 200 ml of EA, adjusted to pH=6–7 using aqueous HCl solution and washed 2 times with 100 ml of a saturated aqueous NaCl solution each time. The organic phase was dried over Na$_2$SO$_4$ and the solvent was removed in vacuo. Chromatography on silica gel using DIP yielded 1.5 g of a colorless oil.

R$_f$(DIP)=0.36 MS(DCI): 328(M+1)$^+$ c) 4'-Cyclohexylidenemethylbiphenyl-2-sulfonylcyanamide 267 mg of 4'-cyclohexylidenemethylbiphenyl-2-sulfonamide were reacted to give the title compound. 80 mg of a pale yellow oil were obtained.

R$_f$(EA/MeOH 10:1)=0.17

EXAMPLE 2

4'-Cyclohexylmethylbiphenyl-2-sulfonylcyanamide

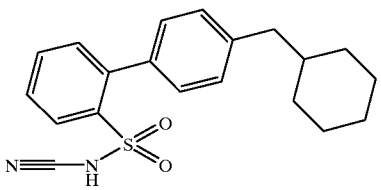

a) 4'-Cyclohexylmethylbiphenyl-2-sulfonamide 1.45 g of 4'-cyclohexylidenemethylbiphenyl-2-sulfonamide were dissolved in 50 ml of MeOH and treated with 200 mg of Pd/C (10%). The mixture was hydrogenated under normal pressure for 20 h under H$_2$ at RT, then the catalyst was filtered off with suction and the solvent was removed in vacuo. 1.4 g of a colorless oil were obtained.

R$_f$(DIP)=0.45 MS(DCI): 330(M+1)$^+$ b) 4'-Cyclohexylmethylbiphenyl-2-sulfonylcyanamide 1.4 g of 4'-cyclohexylmethylbiphenyl-2-sulfonamide were reacted for 2 hours according to the general procedure for the preparation of sulfonylcyanamides from sulfonamides and 1.2 g of a colorless foam were obtained.

R$_f$(EA/MeOH 10:1)=0.31 IR (—C≡N): 2183.1 cm$^{-1}$

The title compounds of Examples 3 and 4 were synthesized analogously to Examples 1 and 2:

EXAMPLE 3

4'-Cyclopentylidenemethylbiphenyl-2-sulfonylcyanamide

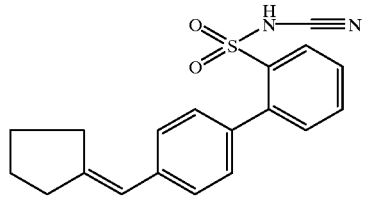

Reacted 1.5 hours; colorless crystals, mp. 115–120° C. with decomposition

R$_f$(EA/MeOH 10:1)=0.18 IR (—C≡N): 2180.3 cm$^{-1}$ MS(ESneg): 337(M-1)$^-$

EXAMPLE 4

4'-Cycloheptylidenemethylbiphenyl-2-sulfonylcyanamide

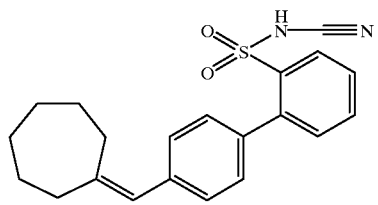

Reacted 1.5 hours; R$_f$(EA/MeOH 10:1)=0.17 IR (—C≡N) :2180.8 cm$^{-1}$ MS(ESneg): 365(M-1)$^-$ mp of potassium salt 168–171° C. with decomposition.

EXAMPLE 5 cis-4'-Styrylbiphenyl-2-sulfonylcyanamide a) 4'-Styrylbiphenyl-2-sulfonamide 9.0 g of benzyltriphenylphosphonium chloride and 2.6 g of KOtBu were stirred at RT for 4 h in 80 ml of anhydrous THF. 3.0 g of 4'-formylbiphenyl-2-sulfonamide were then added and the mixture was stirred at RT for 20 h. 200 ml of a saturated aqueous NaHCO$_3$ solution were added and the mixture was extracted 2 times using 200 ml of EA each time. The organic phase was dried over Na$_2$SO$_4$ and the solvent was removed in vacuo. Chromatography on silica gel using DIP/HEP 1:2 yielded 600 mg of cis-4'-styrylbiphenyl-2-sulfonamide, R$_f$(DIP/HEP 1:2)=0.25 MS(DCI): 336(M+1)$^+$ and 1.2 g of trans-4'-styrylbiphenyl-2-sulfonamide, R$_f$(DIP/HEP 1:2)=0.20 MS(DCI): 336(M+1)$^+$ b) cis-4'-Styrylbiphenyl-2-sulfonylcyanamide 300 mg of cis-4'-styrylbiphenyl-2-sulfonamide were reacted for 2 hours according to the general procedure for the preparation of sulfonylcyanamides from sulfonamides and 249 mg of a colorless foam were obtained.

R$_f$(EA/MeOH 10:1)=0.26 IR (—C≡N): 2182.3 cm$^{-1}$ MS(ESneg): 359(M-1)$^-$ mp of potassium salt 190° C. with decomposition.

EXAMPLE 6 trans-4'-Styrylbiphenyl-2-sulfonylcyanamide

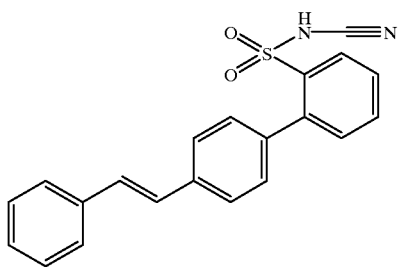

300 mg of trans-4'-styrylbiphenyl-2-sulfonamide were reacted for 2 hours according to the general procedure for the preparation of sulfonylcyanamides from sulfonamides and 290 mg of a colorless foam were obtained.

$R_f$(EA/MeOH 10:1)=0.21 IR (—C≡N): 2180.8 cm$^{-1}$ MS(ESneg): 359(M−1)$^-$ mp of potassium salt 170° C. with decomposition.

EXAMPLE 7

4'-Phenethylbiphenyl-2-sulfonylcyanamide

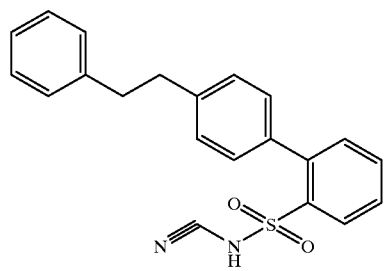

a) 4'-Phenethylbiphenyl-2-sulfonamide 400 mg of 4'-styrylbiphenyl-2-sulfonamide were dissolved in 10 ml of MeOH and 80 mg of Pd/C (10%) were added.

The mixture was hydrogenated under normal pressure for 20 h under H$_2$ at RT, then the catalyst was filtered off with suction and the solvent was removed in vacuo. 350 mg of a colorless oil were obtained.

$R_f$(DIP)=0.46 MS(DCI): 338(M+1)$^+$ b) 4'-Phenethylbiphenyl-2-sulfonylcyanamide 340 mg of 4'-phenethylbiphenyl-2-sulfonamide were reacted for 1 hour according to the general procedure for the preparation of sulfonylcyanamides from sulfonamides and 360 mg of a colorless foam were obtained.

$R_f$(EA/MeOH 10:1)=0.28 IR (—C≡N): 2178.3 cm$^{-1}$

The title compound of Example 8 was synthesized analogously to Example 5:

EXAMPLE 8 cis-4'-(2-Cyclohexylvinyl)biphenyl-2-sulfonylcyanamide

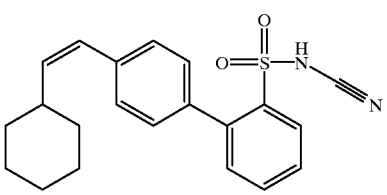

a) cis-4'-(2-Cyclohexylvinyl)biphenyl-2-sulfonamide $R_f$(DIP)=0.45 MS(ES): 342(M+1)$^+$ b) cis-4'-(2-Cyclohexylvinyl)biphenyl-2-sulfonylcyanamide Reaction time: 2 hours; $R_f$(EA/MeOH 10:1)=0.17 IR (—C≡N): 2176.9 cm$^{-1}$ MS(ESneg): 365(M−1)$^-$ mp of potassium salt 189–193° C. with decomposition.

EXAMPLE 9 trans-4'-(2-Cyclohexylvinyl)biphenyl-2-sulfonylcyanamide

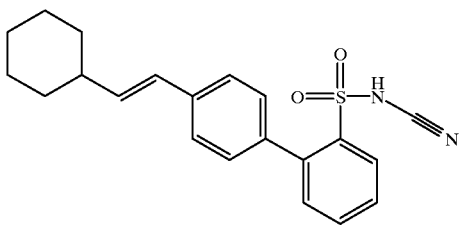

a) trans-4'-(2-Cyclohexylvinyl)biphenyl-2-sulfonamide 1.2 g of cis-4'-(2-cyclohexylvinyl)biphenyl-2-sulfonamide and 894 mg of iodine were dissolved in 100 ml of anhydrous CH$_2$Cl$_2$ and allowed to stand at RT for 5 days. The reaction mixture was diluted with 200 ml of CH$_2$Cl$_2$ and washed 2 times using 100 ml of a saturated aqueous Na$_2$SO$_3$ solution each time. The organic phase was dried over Na$_2$SO$_4$ and the solvent was removed in vacuo. Chromatography on silica gel using DIP yielded 260 mg of a colorless oil.

$R_f$(DIP)=0.45 MS(ES): 342(M+1)$^+$ b) trans-4'-(2-Cyclohexylvinyl)biphenyl-2-sulfonylcyanamide 260 mg of trans-4'-(2-cyclohexylvinyl)biphenyl-2-sulfonamide were reacted for 2 hours according to the general procedure for the preparation of sulfonylcyanamides from sulfonamides and 90 mg of a colorless oil were obtained.

$R_f$(EA/MeOH 10:1)=0.09 IR (—C≡N): 2181.9 cm$^{-1}$ MS(ESneg): 365(M−1)$^-$

EXAMPLE 10

4'-(2-Cyclohexylethyl)biphenyl-2-sulfonylcyanamide

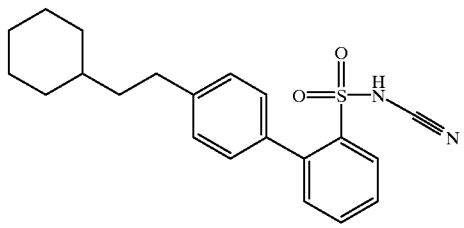

a) 4'-(2-Cyclohexylethyl)biphenyl-2-sulfonamide 800 mg of cis-4'-(2-cyclohexylvinyl)biphenyl-2-sulfonamide were dissolved in 10 ml of MeOH and 80 mg of Pd/C (10%) were added. The mixture was hydrogenated under normal pressure for 5 h under $H_2$ at RT, then the catalyst was filtered off with suction and the solvent was removed in vacuo. 760 mg of a colorless oil were obtained.

$R_f$(DIP)=0.38 MS(DCI): 344(M+1)$^+$ b) 4'-(2-Cyclohexylethyl)biphenyl-2-sulfonylcyanamide 250 mg of 4'-2-cyclohexylethyl)biphenyl-2-sulfonamide were reacted for 3 hours according to the general procedure for the preparation of sulfonylcyanamides from sulfonamides and 90 mg of a colorless oil were obtained.

$R_f$(EA/MeOH 10:1)=0.25 IR (—C≡N): 2178.5 cm$^{-1}$ MS(ESneg): 367(M−1)$^-$ mp of potassium salt: 193° C. with decomposition Pharmacological data:

Inhibition of the Na$^+$-dependent Cl$^-$/HCO$_3^-$ exchanger (NCBE) in human endothelial cells Human endothelial cells (ECV-304) were detached from culture flasks with the aid of trypsin/EDTA buffer (0.05/0.02% in phosphate buffer) and, after centrifugation (100 g, 5 min), taken up in a buffered salt solution (mmol/l: 115 NaCl, 20 NH$_4$Cl, 5 KCl, 1 CaCl$_2$, 1 MgSO$_4$, 20 N-(2-hydroxyethyl)-piperazine-N'-2-ethanesulfonic acid (HEPES), 5 glucose and 1 g/l of bovine serumalbumin; pH 7.4). This cell suspension was incubated at 37° C. for 20 min with 5 µM BCECF acetoxymethyl ester. The cells were then washed and resuspended in a sodium- and bicarbonate-free buffer solution (mmol/l: 5 HEPES, 133.8 choline chloride, 4.7 KCl, 1.25 MgCl$_2$, 0.97 K$_2$HPO$_4$, 0.23 KH$_2$PO$_4$, 5 glucose; pH 7.4).

The subsequent fluorescence measurement in the FLIPR (Fluorescent Imaging Plate Reader), 100 µl of this cell suspension in each case containing 20000 cells were added by pipette per well of a 96-well microtiter plate and this microtiter plate was centrifuged (100 g, 5 min).

In the FLIPR, 100 µl of buffer solution in each case were then removed from a further prepared microtiter plate and added by pipette to each of the 96 wells of the measuring plate. In this case, for a 100% control, i.e. a recovery of the intracellular pH (pH$_i$) by means of the NCBE, a bicarbonate- and sodium-containing buffer solution (mmol/l: 5 HEPES, 93.8 NaCl, 40 NaHCO$_3$, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) which contained 50 µM HOE 642 was used. For a 0% control, i.e. no pH$_i$ recovery at all, a bicarbonate-free, sodium-containing buffer solution (mmol/l: 5 HEPES, 133.8 NaCl, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) to which 50 µM HOE 642 were also added was employed. The compounds of the formula (I) according to the invention were added in various concentrations of the sodium- and bicarbonate-containing solution.

After addition of the buffer solutions to the dye-loaded acidified cells situated in the measuring plate, the increase in the fluorescence intensity which corresponded to an increase in the pH$_i$ was determined in each well of the microtiter plate. The kinetics were in this case recorded at 35° C. over a period of 2 minutes.

The increase in the fluorescence intensities for different concentrations of the compounds according to the invention was related to the two controls and from this the inhibitory action of the substances was determined.

| Results Residual activity of the NCBE at an inhibitor concentration of 10 µM | |
|---|---|
| Example | Residual activity in % |
| 1 | 68.4 |
| 2 | 51.6 |
| 3 | 29.4 |
| 4 | 30.5 |
| 5 | 21.2 |
| 6 | 19.3 |
| 7 | 64.2 |
| 8 | 13.4 |
| 9 | 12.8 |
| 10 | 24.3 |

We claim:

1. A compound of the formula (I),

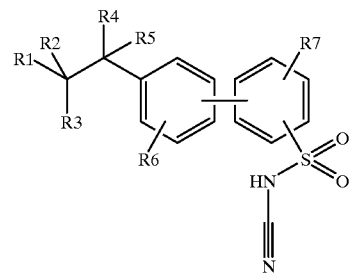

in which the symbols have the following meaning:

R(1) is hydrogen, alkyl having 1,2,3,4,5,6,7 or 8 carbon atoms, 1-naphthyl, 2-naphthyl, —C$_a$H$_{2a}$-cycloalkyl having 3,4,5,6 or 7 carbon atoms or —C$_a$H$_{2a}$-phenyl, where the phenyl moiety is unsubstituted or substituted by 1–3 substituents which are of alkyl having 1,2,3,4,5,6,7 or 8 carbon atoms, F, Cl, Br, I, CF$_3$, SO$_n$R(11), OR(17), NR(8)R(9), —C≡N, —NO$_2$, or CO—R(22);

R(11) is alkyl having 1,2,3, or 4 carbon atoms or NR(20)R(21);

R(20) and R(21) independently of one another are hydrogen or alkyl having 1,2,3 or 4 carbon atoms;

R(17) is hydrogen or alkyl having 1,2,3, or 4 carbon atoms;

R(8) and R(9) independently of one another are hydrogen or alkyl having 1,2,3, or 4 carbon atoms;

R(22) is hydrogen, alkyl having 1,2,3,4,5,6,7, or 8 carbon atoms or OR(30);

R(30) is hydrogen, alkyl having 1,2,3,4,5,6,7, or 8 carbon atoms;

a is zero, 1 or 2;

n is zero, 1 or 2; or

R(1) and R(3) together with the carbon atom bonded to them are cycloalkyl having 3,4,5,6, or 7 carbon atoms or fluorenyl;

R(2), R(3), R(4) and R(5) independently of one another are hydrogen, F, CF$_3$, O—R(10), alkyl having 1,2,3,4, 5,6,7, or 8 carbon atoms, cycloalkyl having 3, 4, 5, 6, or 7 carbon atoms, —$C_gH_{2g}$-phenyl, where the phenyl moiety is unsubstituted or substituted by 1–3 substituents which are F, Cl, Br, I, $CF_3$, methyl, methoxy, hydroxyl, or NR(18)R(19);

R(18) and R(19) independently of one another are hydrogen or alkyl having 1,2,3, or 4 carbon atoms;

g is zero, 1 or 2;

R(10) is hydrogen, alkyl having 1,2,3,4,5,6,7, or 8 carbon atoms, phenyl which is unsubstituted or substituted by 1–3 substituents which are F, Cl, Br, I, $CF_3$, methyl, methoxy, hydroxyl, or NR(12)R(13);

R(12) and R(13) independently of one another are hydrogen or alkyl having 1,2,3, or 4 carbon atoms; or R(10) is heteroaryl having 1,2,3,4,5,6,7,8, or 9 carbon atoms, which is unsubstituted or substituted by 1–3 substituents which are F, Cl, Br, I, $CF_3$, $CH_3$, methoxy, hydroxyl or NR(14)R(15);

R(14) and R(15) independently of one another are hydrogen or alkyl having 1,2,3, or 4 carbon atoms; or R(2) and R(4) together are a second bond between the carbon atoms bonded to the radicals R(3) and R(5) where R(1), R(3), and R(5) are as defined above;

R(6) and R(7) independently of one another are hydrogen, F, Cl, Br, I, $CF_3$, —C≡N, —$NO_2$, $SO_p$—R(16), CO—R(23), or O—R(24);

R(23) is hydrogen, alkyl having 1,2,3,4,5,6,7, or 8 carbon atoms or OR(25);

R(25) is hydrogen, alkyl having 1,2,3,4,5,6,7, or 8 carbon atoms;

R(24) is hydrogen, alkyl having 1,2,3,4,5,6,7, or 8 carbon atoms or phenyl, which is unsubstituted or substituted by 1–3 substituents which are F, Cl, Br, I, $CF_3$, methyl, methoxy, hydroxyl, or NR(28)R(29);

R(28) and R(29) are H or alkyl having 1,2,3, or 4 carbon atoms;

R(16) is alkyl having 1,2,3,4,5,6,7 or 8 carbon atoms, phenyl which is unsubstituted or substituted by 1–3 substituents which are F, Cl, Br, I, $CF_3$, methyl, methoxy, hydroxyl or NR(26)R(27);

R(26) and R(27) are H or alkyl having 1,2,3 or 4 carbon atoms;

p is zero, 1 or 2;

or its physiologically tolerable salts.

2. A compound of the formula (I) as claimed in claim 1, in which:

R(1) is hydrogen, alkyl having 1,2,3 or 4 carbon atoms, 1-naphthyl, 2-naphthyl, —$C_aH_{2a}$-cycloalkyl having 3, 4, 5, 6 or 7 carbon atoms or —$C_aH_{2a}$-phenyl, where the phenyl moiety is unsubstituted or substituted by 1–2 substituents which are alkyl having 1,2,3 or 4 carbon atoms, F, Cl, $CF_3$, $SO_nR(11)$, OR(17), NR(8)R(9), —C≡N, or CO—R(22);

R(11) is alkyl having 1,2,3 or 4 carbon atoms or NR(20)R(21);

R(20) and R(21) independently of one another are hydrogen, methyl or ethyl;

R(17) is hydrogen or alkyl having 1,2,3 or 4 carbon atoms;

R(8) and R(9) independently of one another are hydrogen, methyl or ethyl;

R(22) is hydrogen, alkyl having 1,2,3 or 4 carbon atoms or OR(30);

R(30) is hydrogen, alkyl having 1,2,3 or 4 carbon atoms;

a is zero or 1;

n is zero or 2; or

R(1) and R(3) together with the carbon atom bonded to them are cycloalkyl having 3, 4, 5, 6 or 7 carbon atoms or fluorenyl;

R(2) and R(4) independently of one another are hydrogen or F; or

R(2) and R(4) together are a second bond between the carbon atoms bonded to the radicals R(3) and R(5);

R(3) and R(5) independently of one another are hydrogen, F, $CF_3$, O—R(10), alkyl having 1,2,3 or 4 carbon atoms, cycloalkyl having 3, 4, 5, 6 or 7 carbon atoms, —$C_gH_{2g}$-phenyl, where the phenyl moiety is unsubstituted or substituted by 1–2 substituents which are F, Cl, $CF_3$, methyl, methoxy, hydroxyl or NR(18)R(19);

R(18) and R(19) independently of one another are hydrogen, methyl, or ethyl;

g is zero or 1;

R(10) is hydrogen, alkyl having 1, 2, 3 or 4 carbon atoms, phenyl which is unsubstituted or substituted by 1–2 substituents which are F, Cl, $CF_3$, methyl, methoxy, hydroxyl or NR(12)R(13);

R(12) and R(13) independently of one another are hydrogen, methyl or ethyl; or

R(10) is heteroaryl having 1, 2, 3, 4, 5, 6, 7, 8, or 9 carbon atoms, which is unsubstituted or substituted by 1–2 substituents which are F, Cl, $CF_3$, $CH_3$, methoxy, hydroxyl or NR(14)R(15);

R(14) and R(15) independently of one another are hydrogen, methyl, or ethyl;

R(6) and R(7) independently of one another are hydrogen, F, Cl, $CF_3$, —C≡N, $SO_p$—R(16), CO—R(23), or O—R(24);

R(23) is hydrogen, alkyl having 1,2,3, or 4 carbon atoms or OR(25);

R(25) is hydrogen, alkyl having 1,2,3, or 4 carbon atoms;

R(24) is hydrogen, alkyl having 1,2,3 or 4 carbon atoms or phenyl which is unsubstituted or substituted by 1–2 substituents which are F, Cl, $CF_3$, methyl, methoxy, hydroxyl, or NR(28)R(29);

R(28) and R(29) independently of one another are hydrogen, methyl, or ethyl;

R(16) is alkyl having 1,2,3 or 4 carbon atoms or phenyl which is unsubstituted or substituted by 1–2 substituents which are F, Cl, $CF_3$, methyl, methoxy, hydroxyl, or NR(26)R(27);

R(26) and R(27) independently of one another are hydrogen, methyl, or ethyl;

p is zero or 2;

or a physiologically tolerable salt.

3. A compound of the formula (I) as claimed in claim 1 or 2, in which:

R(1) is methyl, ethyl, 1-naphthyl, 2-naphthyl, —$C_aH_{2a}$-cycloalkyl having 3, 4, 5, 6 or 7 carbon atoms or —$C_aH_{2a}$-phenyl, where the phenyl moiety is unsubstituted or substituted by 1–2 substituents which are alkyl having 1,2,3 or 4 carbon atoms, F, Cl, $CF_3$, $SO_2R(11)$, OR(17), NR(8)R(9), —C≡N, or CO—R(22);

R(11) is methyl or dimethylamino;

R(17) is hydrogen, methyl or ethyl;

R(8) and R(9) independently of one another are hydrogen, methyl or ethyl,

R(22) is hydrogen or alkyl having 1,2,3 or 4 carbon atoms;

a is zero or 1; or

R(1) and R(3) together with the carbon atom carrying them are cycloalkyl having 3,4,5,6 or 7 carbon atoms or fluorenyl;

R(2) and R(4) independently of one another are hydrogen or F; or

R(2) and R(4) together are a second bond between the carbon atoms bonded to the radicals R(3) and R(5).

R(3) and R(5) independently of one another are hydrogen, F, $CF_3$, O—R(10), alkyl having 1,2,3 or 4 carbon atoms or —$C_gH_{2g}$-phenyl which is unsubstituted or substituted by 1–2 substituents which are F, Cl, $CF_3$, methyl, methoxy, hydroxyl or NR(18)R(19);

R(18) and R(19) independently of one another are hydrogen, methyl or ethyl;

g is zero or 1;

R(10) is hydrogen, alkyl having 1,2,3 or 4 carbon atoms or phenyl which is unsubstituted or substituted by 1–2 substituents which are F, Cl, $CF_3$, methyl, methoxy, hydroxyl or NR(12)R(13);

R(12) and R(1 3) are hydrogen, methyl or ethyl; or

R(10) is heteroaryl having 1,2,3,4,5,6,7,8 or 9 carbon atoms, which is unsubstituted or substituted by 1–2 substituents which are F, Cl, $CF_3$, $CH_3$, methoxy, hydroxyl or dimethylamino;

R(6) and R(7) independently of one another are hydrogen, F, Cl, $CF_3$, —C≡N, $SO_2$—R(16), CO—R(23) or O—R(24);

R(23) is hydrogen or alkyl having 1, 2, 3 or 4 carbon atoms;

R(24) is hydrogen, alkyl having 1,2,3 or 4 carbon atoms or phenyl which is unsubstituted or substituted by 1–2 substituents which are F, Cl, $CF_3$, methyl, methoxy, hydroxyl or NR(28)R(29);

R(28) and R(29) independently of one another are hydrogen, methyl or ethyl;

R(16) is alkyl having 1,2,3, or 4 carbon atoms;

or a physiologically tolerable salt.

4. A compound of the formula (I) as claimed in claim 3, in which:

R(1) is methyl, ethyl, 1-naphthyl, 2-naphthyl, cycloalkyl having 3, 4, 5, 6 or 7 carbon atoms or phenyl which is unsubstituted or substituted by a substituent which is alkyl having 1,2,3 or 4 carbon atoms, F, Cl, $CF_3$, $SO_2R(11)$, OR(17), NR(8)R(9), or CO—R(22);

R(11) is methyl or dimethylamino;

R(17) is hydrogen, methyl or ethyl;

R(8) and R(9) independently of one another are hydrogen, methyl or ethyl;

R(22) is hydrogen or alkyl having 1,2,3, or 4 carbon atoms; or

R(1) and R(3) together with the carbon atom bonded to carrying them are cycloalkyl at having 3, 4, 5, 6 or 7 carbon atoms or fluorenyl;

R(2) and R(4) are hydrogen; or

R(2) and R(4) together are a second bond between the carbon atoms bonded to the radicals R(3) and R(5);

R(3) and R(5) independently of one another are hydrogen, $CF_3$, O—R(10), alkyl having 1, 2, 3 or 4 carbon atoms or phenyl which is unsubstituted or substituted by a substituent which is F, Cl, $CF_3$, methyl, methoxy, hydroxyl or NR(18)R(19);

R(18) and R(19) independently of one another are hydrogen, methyl, or ethyl;

R(10) is hydrogen, alkyl having 1,2,3 or 4 carbon atoms or phenyl which is unsubstituted or substituted by 1 substituent which is F, Cl, $CF_3$, methyl, methoxy, hydroxyl or NR(12)R(13);

R(12) and R(13) independently of one another are hydrogen, methyl or ethyl, or

R(10) is heteroaryl having 1, 2, 3, 4, 5, 6, 7, 8 or 9 carbon atoms, which is unsubstituted or substituted by a substituent which is F, Cl, $CF_3$, $CH_3$, methoxy, hydroxyl or dimethylamino;

R(6) and R(7) independently of one another are hydrogen, F, Cl, $CF_3$, $SO_2$—$CH_3$, CO—R(23) or O—R(24);

R(23) is hydrogen or alkyl having 1,2,3, or 4 carbon atoms;

R(24) is hydrogen, alkyl having 1,2,3 or 4 carbon atoms or phenyl which is unsubstituted or substituted by 1 substituent which is F, Cl, $CF_3$, methyl, methoxy, hydroxyl or NR(28)R(29);

R(28) and R(29) independently of one another are hydrogen, methyl, or ethyl;

or a physiologically tolerable salt.

5. A method for the treatment or prophylaxis of illnesses caused by ischemic conditions in a patient in need thereof, comprising administering an effective amount of a compound of claim 1 to the patient.

6. A method for the treatment or prophylaxis of ischemic conditions in a patient in need thereof, comprising administering an effective amount of a compound of claim 1 to the patient.

7. A method for the treatment or prophylaxis of ischemic conditions according to claim 6, wherein the ischemic condition is of the heart, peripheral and central nervous systems, or peripheral organs and members.

8. A method for the treatment or prophylaxis of impaired respiratory drive in a patient in need thereof, comprising administering an effective amount of a compound of claim 1 to the patient.

9. A method for the treatment or prophylaxis of cardiac infarction in a patient in need thereof, comprising administering an effective amount of a compound of claim 1 to the patient.

10. A method for the treatment or prophylaxis of angina pectoris in a patient in need thereof, comprising administering an effective amount of a compound of claim 1 to the patient.

11. A method for the treatment or prophylaxis of stroke in a patient in need thereof, comprising administering an effective amount of a compound of claim 1 to the patient.

12. A method for the treatment of states of shock in a patient in need thereof, comprising administering an effective amount of a compound of claim 1 to the patient.

13. A method for storing transplants for surgical measures, comprising storing a transplant in a solution comprising an effective amount of a compound of claim 1.

14. A method for the treatment of illnesses in which cell proliferation is a primary or secondary cause in a patient in need thereof, comprising administering an effective amount of a compound of claim 1 to the patient.

15. A pharmaceutical composition, comprising a compound of claim 1 together with a pharmaceutically acceptable carrier.

16. A pharmaceutical composition according to claim 15, further comprising an effective amount of an NHE inhibitor, a physiologically tolerable salt thereof, or both.

17. A pharmaceutical composition according to claim 15, further comprising another cardiovascular active compound, a physiologically tolerable salt thereof, or both.

18. A pharmaceutical composition according to claim 16, further comprising another cardiovascular active compound, a physiologically tolerable salt thereof, or both.

* * * * *

UNITED STATES PATENT AND TRADEMARK OFFICE
CERTIFICATE OF CORRECTION

PATENT NO.: 5,968,978

DATED: October 19, 1999

INVENTORS: Heinz-Werner KLEEMANN et al.

It is certified that an error appears in the above-identified patent and that said Letters Patent is hereby corrected as shown below:

Claim 3, Column 23, line 19, "R(1 3)" should read --R(13)--.

Claim 4, Column 23, line 52, after "cycloalkyl", delete "at".

Signed and Sealed this

Twenty-fifth Day of July, 2000

Attest:

Q. TODD DICKINSON

*Attesting Officer*  *Director of Patents and Trademarks*